(12) United States Patent
Wang et al.

(10) Patent No.: US 8,877,951 B2
(45) Date of Patent: Nov. 4, 2014

(54) ACID-FUNCTIONALIZED NANOPARTICLE CATALYST AND CATALYZED REACTIONS USING THE SAME

(71) Applicant: Kansas State University Research Foundation, Manhattan, KS (US)

(72) Inventors: Hongwang Wang, Manhattan, KS (US); Stefan Bossmann, Manhattan, KS (US); Byungjun Kollbe Ahn, Goleta, CA (US); Xiuzhi Susan Sun, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 14/351,786

(22) PCT Filed: Oct. 24, 2012

(86) PCT No.: PCT/US2012/061595
§ 371 (c)(1), (2), (4) Date: Apr. 14, 2014

(87) PCT Pub. No.: WO2013/063047
PCT Pub. Date: May 2, 2013

(65) Prior Publication Data
US 2014/0275583 A1 Sep. 18, 2014

Related U.S. Application Data

(60) Provisional application No. 61/550,732, filed on Oct. 24, 2011.

(51) Int. Cl.
*B01J 31/28* (2006.01)
*C07D 307/48* (2006.01)

(52) U.S. Cl.
CPC .............. *B01J 31/28* (2013.01); *C07D 307/48* (2013.01)
USPC ........................................................ 549/498

(58) Field of Classification Search
USPC ........................................................ 549/498
See application file for complete search history.

(56) References Cited

U.S. PATENT DOCUMENTS
2010/0092841 A1  4/2010  Lopez et al.

FOREIGN PATENT DOCUMENTS
KR  1020070059975  6/2007

OTHER PUBLICATIONS

International Search Report and Written Opinion dated Jan. 30, 2013 in the corresponding PCT/US2012/061595 filed Oct. 24, 2012.
Ahn, Kollbe B. "Ring Opening of Epoxidized Methyl Oleate Using a Novel Acid-Functionalized Iron Nanoparticle Catalyst" Green Chem., 2012, pp. 136-142, V.14.
Kassaee, M.Z. "Sulfamic Acid-Functionalized Magnetic Fe3O4 Nanopraticles as an Efficient and Reusable Catalyst for One-Pot Synthesis of Alfa-Amino Nitriles in Water" Applied Catalysis A: General, 2011 pp. 28-33, V.395.
Melero, Juan A. "Biodiesel Production from Crude Palm Oil Using Sulfonic Acid-Modified Mesostructured Catalysts" Chemical Engineering Journal, 2010, pp. 323-331, V. 161.
De Palma, Randy "Silane Ligand Exchange to Make Hydrophobic Superparamagnetic Nanoparticles Water-Dispersible" Chem. Mater, 2007, pp. 1821-1831, V. 19.

*Primary Examiner* — Kristin Vajda
(74) *Attorney, Agent, or Firm* — Hovey Williams LLP (57) ABSTRACT

Superparmagnetic acid-functionalized nanoparticle catalysts are provided along with methods of using the same to protonate an oxygen atom of a carbon-oxygen bond. Particularly, the catalysts comprise a nanoparticle having a ferromagnetic core surrounded by a metal oxide shell. The nanoparticle is at least partially coated with an acid-functionalized siloxane compound. The acid-functionalized nanoparticles may be used to catalyze any number of reactions that can be catalyzed in the presence of protons. The ferromagnetic core permits the nanoparticle catalyst material to be separated from the reaction medium through application of a magnetic field and reused.

20 Claims, 11 Drawing Sheets

ACID-FUNCTIONALIZED NANOPARTICLE CATALYST AND CATALYZED REACTIONS USING THE SAME

CROSS-REFERENCE TO RELATED APPLICATIONS

The present application claims the benefit of and priority from U.S. Provisional Patent Application Ser. No. 61/550,732, filed Oct. 24, 2011, the entire disclosure of which is hereby incorporated by reference herein.

FEDERALLY SPONSORED RESEARCH OR DEVELOPMENT

This invention was made with government support under Award No. EPS-0903806 by the National Science Foundation (NSF). The United States government has certain rights in the invention.

BACKGROUND OF THE INVENTION

1. Field of the Invention

The present invention is generally directed toward an acid-functionalized nanoparticle and uses thereof as catalysts in hydrolysis reactions, particularly in ring opening of epoxidized plant oils such as epoxidized soybean oils and the conversion of cellulose into fructose and 2,5-dimethyl-furan.

2. Description of the Prior Art

Epoxidized soybean oil (ESO), a well-known and commercially available functionalized plant oil as a plasticizer in the plastics industry, is amenable to hydrolysis using conventional chemical methodology of ring-opening reaction of oxirane moieties. Hydroxyl soybean oil called soy polyol is produced from ESO via α-methoxy-hydroxylation and is widely used for polyurethane applications. Plant oil-based polyol show better environmental benefits than petroleum-based polyols because of the former's significantly lowered greenhouse gas emissions.

The global market for polyols is forecasted to reach 4 billion pounds by the year 2015. Recently, Recticel (Evere, Belgium), the largest polyurethane manufacturer in Europe, has started to produce foams using BiOH® (Cargill Inc., Minneapolis, Minn.). Although soy polyols were derived from biobased feedstocks, synthetic methods for most soy polyol production do not emphasize green chemistry, which has been spotlighted recently because of stricter government regulations regarding sustainability.

The term green chemistry was comprehensively defined by Anastas and Warner as "the utilization of a set of principles that reduces or eliminates the use or generation of hazardous substance in the design, manufacture and application of chemical products" with 12 principles: 1) prevention, 2) atom economy, 3) less hazardous chemical syntheses, 4) safer chemicals, 5) safer solvents and auxiliaries, 6) energy efficiency, 7) use of renewable feedstocks, 8) derivatives reduction, 9) catalysis, 10) design for degradation, 11) real-time analysis for pollution prevention, and 12) inherently safer chemistry for accident prevention. In terms of green chemistry, a common problem in the synthesis of α-methoxy-hydroxylation from epoxidized oleo-chemicals is the need for strong Brønsted acids to activate the epoxide ring toward the attack of weakly nucleophilic alcohols. This has been accomplished through the action of strong homogeneous acids such as HCl, HBr, or p-toluenesulfonic acid. Even formic acid (a milder acid) has been shown to accomplish one-pot synthesis of soy polyols, although this reaction presented low reaction selectivity (non-homogeneous distribution and oligomerization) and low conversion yield (residual epoxides). All cases require the removal of acid, solvent purification steps, and high temperature, which generates carbon emissions and undesirable byproducts such as ketones. Green chemistry researchers have become interested in solid acid catalysts (e.g., zeolites, heteropolyacids, and ion-exchange resins), which, if they replaced the numerous tons of non-recyclable homogeneous acid catalysts consumed annually in current industrial processes, would minimize environmental defects including waste generation.

Heterogeneous catalysts have shown potential as replacements for traditional homogeneous acid-catalyzed processes, including biodiesel production. Rios et al. presented ring opening of epoxidized methyl oleate using commercial heterogeneous acid resin catalysts such as SAC 13 and Amberlite 15; however, the commercial heterogeneous solid catalysts recorded lower product yield and higher energy consumption than homogeneous sulfuric acid in the ring opening of epoxidized methyl oleate (EMO). See, L. A. Rios, et al., Appl. Catal., A, 2005, 284, 155-161. Increased activity and stability has been shown using sulfonic acid-functionalized mesostructured silica, this technique carries the inconvenience of the resin swelling.

SUMMARY OF THE INVENTION

In one embodiment of the present invention a catalyst material is provided. The catalyst generally comprises a plurality of nanoparticles having a ferromagentic core and a metal oxide shell covering at least a portion of the outer surface of the core. A siloxane compound having a nucleophilic functional group is provided on the particles. Particularly, the siloxane compound at least partially coats the nanoparticles and provides a protective layer for the nanoparticles. The nucleophilic functional group of the siloxane compound is itself functionalized with an acidic group.

In certain preferred forms, the catalyst material comprises an $Fe/Fe_3O_4$ core/shell configuration. The nanoparticle is then treated so as to provide an aminofunctional or mercaptofunctional siloxane layer, to which an acidic group may be attached, thereby providing an acid-functionalized nanoparticle catalyst material. The addition of the siloxane layer causes the nanoparticles to assume a core/shell/shell configuration. The acidic group which is attached to the nucleophilic site of the siloxane compound may comprise sulfamic acid, any number of carboxylic acids, and sulfonic acid.

In another embodiment according to the present invention methods of protonating an oxygen atom involved in a carbon-oxygen bond in an organic compound is provided. Generally, the methods comprise providing a mixture including an organic compound having one or more carbon-oxygen bonds and an acid-functionalized nanoparticle catalyst as described herein. The mixture is subjected to conditions in which at least one oxygen atom involved in one of the carbon-oxygen bonds is protonated thereby forming a hydrolyzed product.

Exemplary reactions which employ catalysts according to the present invention include ring opening of epoxidized plant oils and hydrolysis of cellulosic materials. In one such reaction, epoxidized soybean oil is hydrolyzed into soy polyols, which be used in the manufacture of polyurethanes. In another reaction, cellulosic biomass can be reacted in the presence of the acid-functionalized nanoparticle catalyst to hydrolyze glycosidic bonds thereby producing C6 sugars such as glucose and fructose. These sugars are useful precursors in the production of biofuel compounds such as 2,5-dimethyl-furan.

DETAILED DESCRIPTION OF THE PREFERRED EMBODIMENT

Catalysts according to the present invention generally comprise nanoparticles having an inorganic core. The term "nanoparticle" as used herein refers to particles with average particle sizes of under 100 nm. In particular embodiments, the nanoparticles comprise a metal or metal alloy core and a magnetite shell that at least partially surrounds the core. In preferred embodiments of the present invention, the core comprises a member selected from the group consisting of Au, Ag, Cu, Co, Fe, Pt, Ni, and alloys thereof. However, in many embodiments, it is preferable that the core comprise a ferromagetic metal, especially Fe. Also, in certain embodiments, it is understood that the metal from which the core is comprised is in elemental (i.e., uncompounded or zero valent) form, such as $Fe^0$.

In certain embodiments according to the present invention, the shell material that at least partially surrounds, and more preferably completely envelops the core, comprises one or more members selected from the group consisting of Ag, Cu, Co, Fe, Mn, Ni, and the metal oxides (e.g., FeO, $Fe_3O_4$, $Fe_2O_3$, $Fe_xO_y$ (non-stoichiometric iron oxide), CuO, $Cu_2O$, NiO, $Ag_2O$, $Mn_2O_3$) thereof. Exemplary nanoparticles used in a catalyst material according to the present invention are $Fe/Fe_3O_4$ core shell nanoparticles. Synthesis of exemplary $Fe/Fe_3O_4$ nanoparticles is further described in the examples below.

In certain embodiments, the nanoparticles have an average total diameter of from about 1 nm to about 100 nm, from about 2 nm to about 20 nm, or from about 3 nm to about 10 nm. The core of the nanoparticles may have an average diameter of from about 0.5 nm to about 99 nm, from about 1 nm to about 18 nm, or from about 2 nm to about 9 nm. The shell of the nanoparticles may have an average thickness of about 0.5 nm to about 10 nm, or about 1 nm to about 2 nm. In certain embodiments, the nanoparticles have a Brunauer-Emmett-Teller (BET) multipoint surface area of about 20 $m^2/g$ to about 500 $m^2/g$, about 50 $m^2/g$ to about 350 $m^2/g$, or about 60 $m^2/g$ to about 80 $m^2/g$. The nanoparticles may also have a Barret-Joyner-Halenda (BJH) adsorption cumulative surface area of pores having a width between 17.000 Å and 3000.000 Å of about 20 $m^2/g$ to about 500 $m^2/g$, or about 50 $m^2/g$ to about 150 $m^2/g$. The nanoparticles may also have a BJH desorption cumulative surface area of pores having a width between 17.000 Å and 3000.000 Å of about 50 $m^2/g$ to about 500 $m^2/g$, or about 50 $m^2/g$ to about 150 $m^2/g$. The nanoparticle population may also be substantially monodisperse, with a very narrow size/mass size distribution. In certain embodiments, the nanoparticle population has a polydispersity index of about 1.2 to about 1.05. In some embodiments, the nanoparticles used in the inventive catalyst comprise discrete particles. The discrete nanoparticles may exhibit some clustering, but in some embodiments, clustering is to be avoided.

A protective siloxane compound may be applied or coated onto at least a portion of the core/shell nanoparticle. The siloxane compound comprises a functional group that provides a nucleophile for facilitating attachment of another functional group, such as an acidic functional group. In certain embodiments, the siloxane compound comprises a coating for the nanoparticle having an average thickness of between about 0.1 nm to about 10 nm, between about 1 nm to about 5 nm, or between about 1.5 to about 3.5 nm. However, the thickness of the siloxane compound layer can be varied depending upon the specific end use for the catalyst material. Thus, the coated nanoparticle assumes a magnetic core/shell/shell configuration. In certain embodiments, the siloxane compound comprises an aminofunctional siloxane or a mercaptofunctional siloxane.

Exemplary aminofunctional siloxanes suitable for use with the present invention include 3-aminopropyltriethoxysilane, 3-aminopropyltrimethoxysilane, 3-(trimethoxysilyl)propanenitrile, and 3-(triethoxysilyl)propanenitrile. Exemplary mercaptofunctional siloxane compounds include 3-thiopropyltriethoxysilane (TPTES), 3-thiopropyltrimethoxysilane, 3,3,12,12-tetramethoxy-2,13-dioxa-7,8-dithia-3,12-disilatetradecane and 3,3,12,12-tetraethoxy-2,13-dioxa-7,8-dithia-3,12-disilatetradecane. Suitable siloxanes can be purchased, or they can be synthesized via known methods (i.e., aminolysis of chloroalkyltrimethoxysilanes or hydrogenation of cyanoalkyltrimethoxysilanes). Once coated on to the nanoparticles, the terminal alkylamine groups of the aminofunctional siloxanes or the terminal mercapto groups of the mercaptofunctional siloxanes can be used as nucleophiles for the attachment of acidic groups capable of catalyzing certain desired reactions.

The introduction of acidic groups on the surface of the nanoparticles can be performed as a single step reaction because of the presence of the nucleophilic groups on the outer surface of the particle. Thus, the acid-functionalized nanoparticles can be synthesized in fewer steps and at lower cost compared to other acid-functionalized nanoparticle catalysts, such as silica-coated catalysts. For example, with sulfamic acid-functionalized, silica-coated particles, a SH group must be introduced onto the surface of the particle and then oxidized to $SO_3H$ using a concentrated $H_2O_2$ solution, followed by multiple washing steps.

Figure 1:
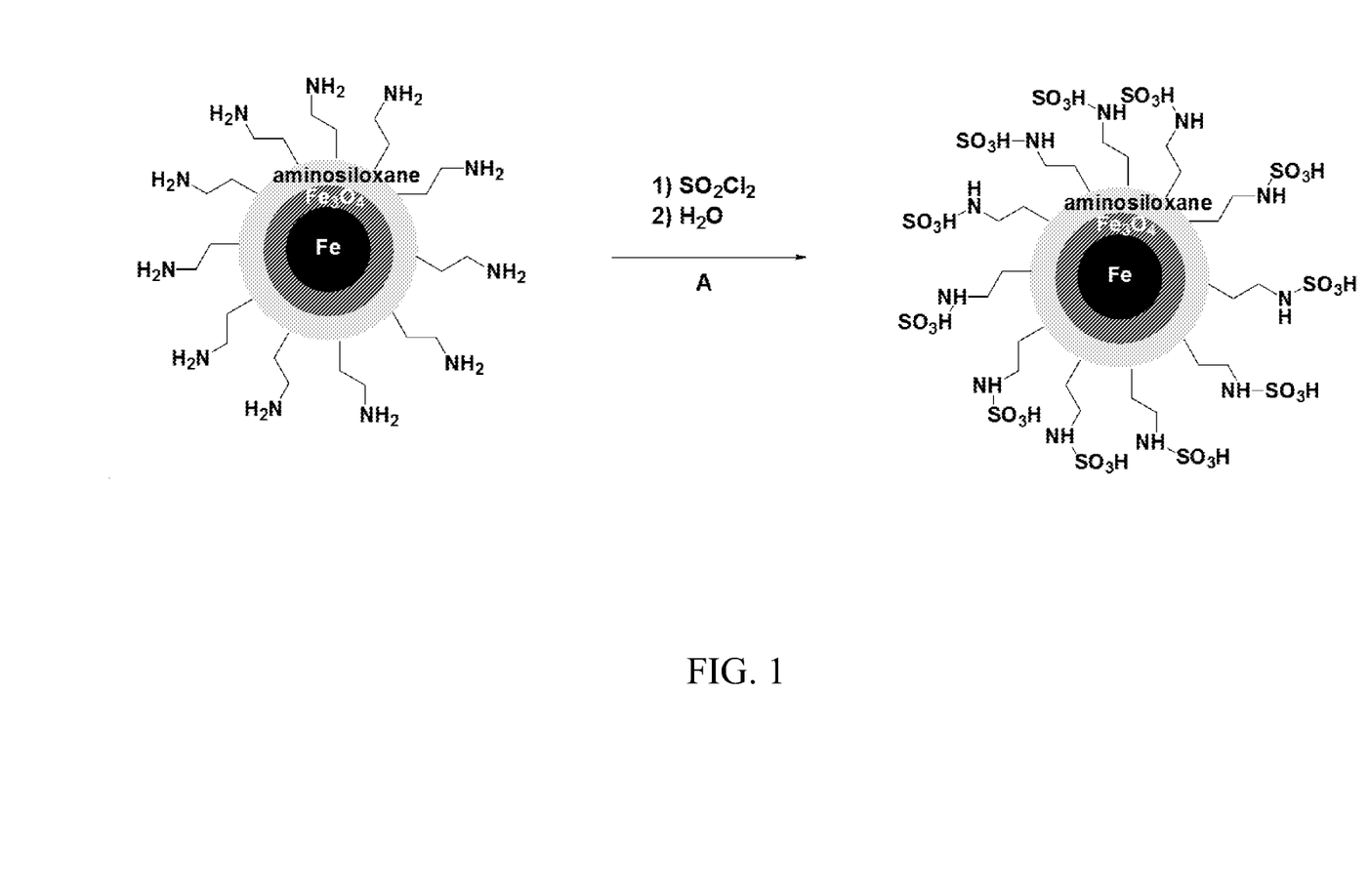
FIG. 1 is a schematic depiction of attachment of sulfamic acid groups to an aminosiloxane-coated nanoparticle by reaction with sulfuryl chloride and subsequent hydrolysis.

In one embodiment according to the present invention, the siloxane layer may be functionalized with sulfamic acid by reaction with sulfuryl chloride and subsequent hydrolysis. This reaction scheme is depicted in FIG. 1. Sulfamic acids generally have a pKa value of about 1.0, which is higher than certain sulfonic acids that have pKa values of about −2. Many catalytic reactions, such as the ring-opening of epoxides, require general acid catalysis and not specific acid catalysis. The somewhat weaker sulfamic acid functional groups enable general and specific acid catalysis mechanisms. Therefore, the sulfamic acid-functionalized catalysts tend to be more versatile than sulfonic acid-functionalized catalysts lending themselves toward a much broader range of applications.

Figure 2:
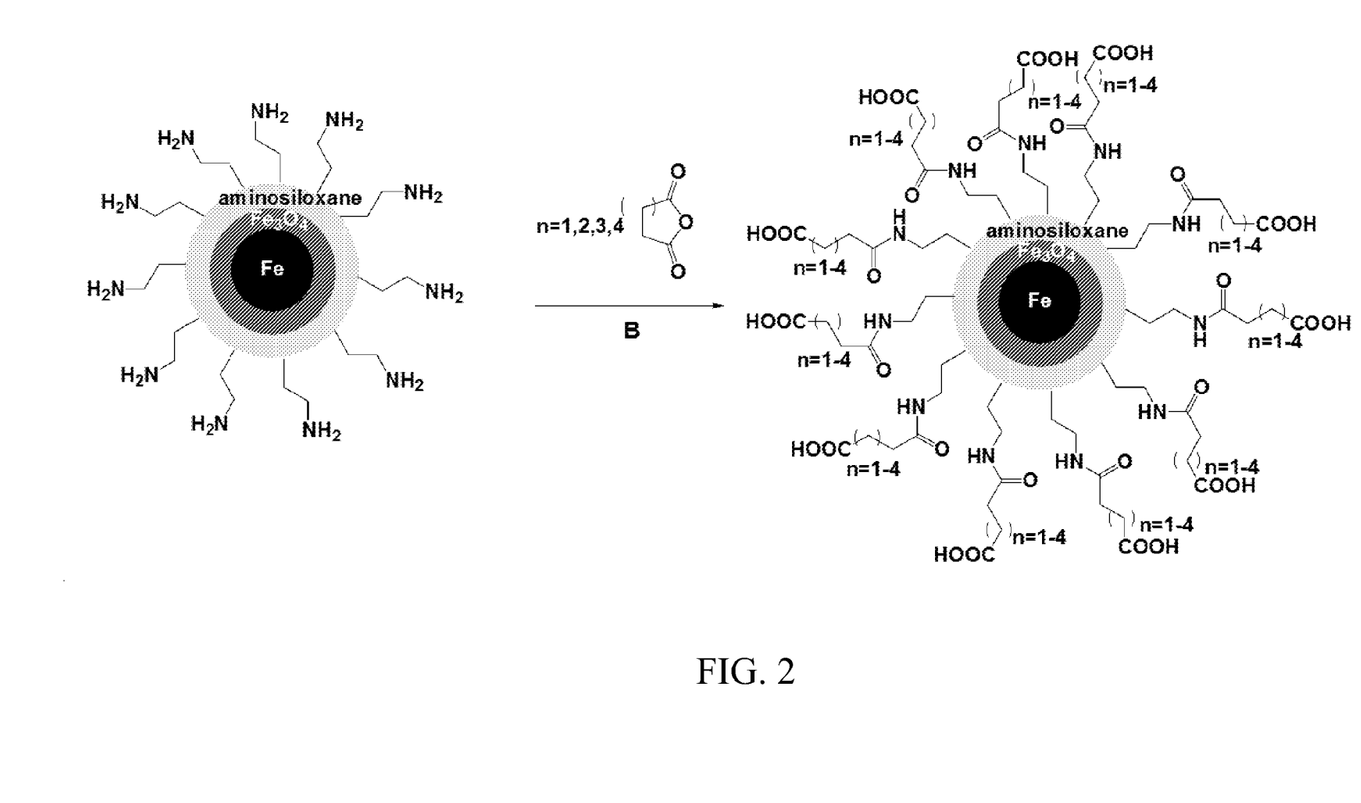
FIG. 2 is a schematic depiction of attachment of carboxylic acid groups to an aminosiloxane-coated nanoparticle by reaction with carboxylic acid anhydrides.

As depicted in FIG. 2, the siloxane layer may be functionalized with carboxylic acid groups by reaction with carboxylic acid anhydrides. In certain embodiments, the carboxylic acid group attached to the nucleophilic group of the siloxane layer is a C2-C10 carboxylic acid or anhydride thereof. In particular embodiments, the carboxylic acid may be succinic acid, glutaric acid, adipic acid, or heptanedioic acid, or anhydrides thereof.

Figure 3:
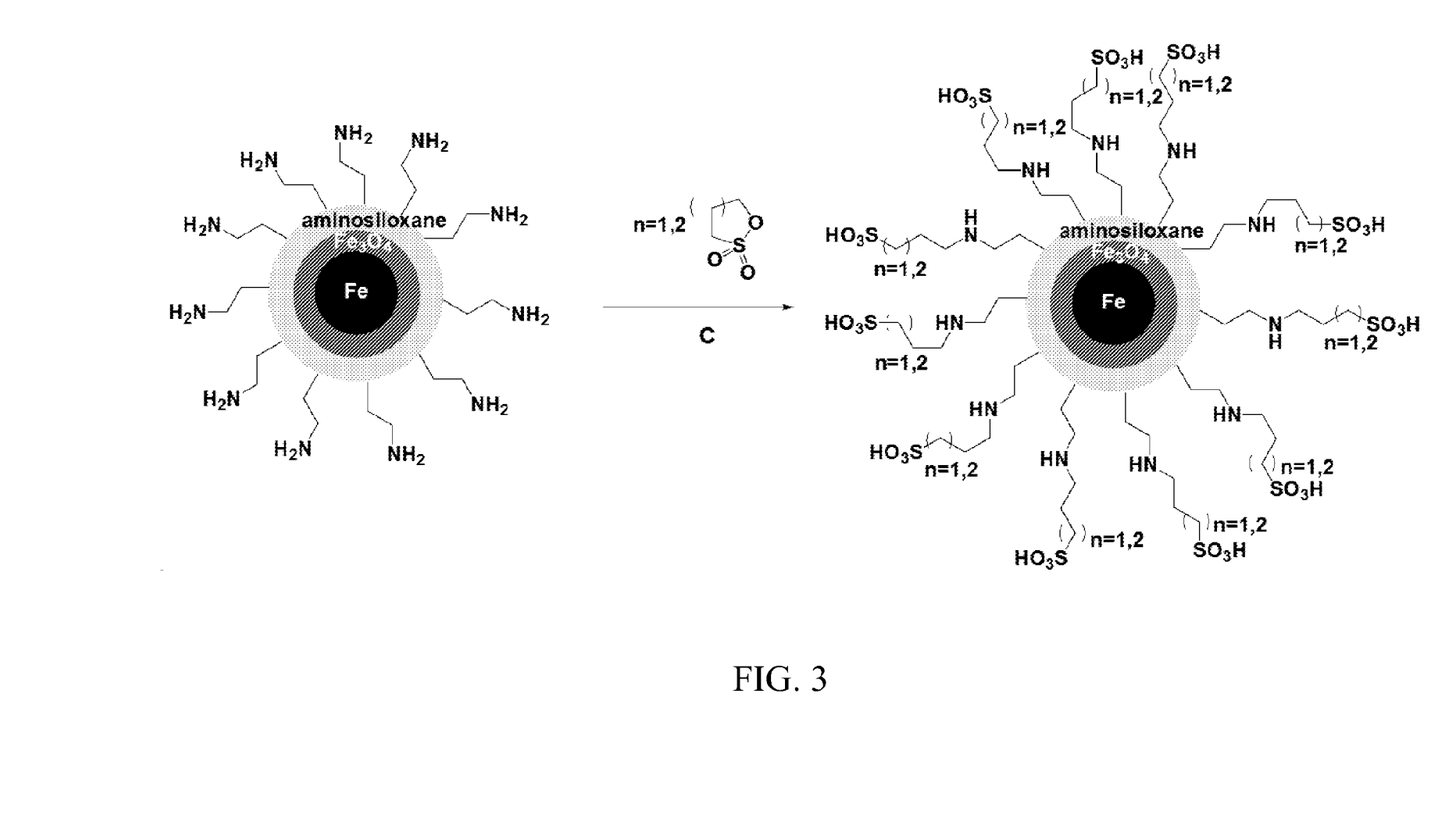
FIG. 3 is a schematic depiction of attachment of sulfonic acids to an aminosiloxane-coated nanoparticle by reaction with propane-sultone or butane-sultone.

Further, as depicted in FIG. 3, the siloxane layer may be functionalized with sulfonic acids by reaction with a sultone. In certain embodiments, the sultone may be propane-sultone or butane-sultone. During functionalization, the sultone ring opens and becomes attached to the nucleophilic group of the siloxane layer.

The magnetic core/shell/shell nanocatalysts with acidic groups can be used for virtually any reaction that can be catalyzed in the presence of protons. Inapposite to mineral acids (e.g. sulfuric acid or hydrochloric acid), the acidic catalyst can be recycled after the reaction is completed by magnetically-aided collection of the nanoparticles. The ferromagentic (e.g., Fe(0)) core is designed to withstand rather harsh reaction conditions (i.e., temperatures of up to about 250° C., or even up to about 300° C. in the absence of oxygen, for 5 hours) for at least 25 consecutive applications. Reduction of previously oxidized core/shell/shell nanocatalysts with conventional reduction agents (e.g. hydrazine, $NaBH_4$ or $H_2$) is possible thus enabling the recycling of the nanocatalysts.

In particular embodiments according to the present invention, the acid-functionalized nanoparticle catalysts can be employed to protonate an oxygen atom involved in a carbon-oxygen bond, especially the protonation of an oxygen atom in an epoxide (oxirane) or in the glycosidic bond between two glucose molecules (in cellulose) thereby leading to a rapid consecutive reaction (nucleophilic reaction with an alcohol or water). Protonation of a glucose molecule (after hydrolysis of cellulose) leads to the observed isomerization to fructose and then to the dehydration to 5-hydroxymethyl-furfural (5-HMF), a feedstock in the production of biofuels.

In one particular aspect, the acid-functionalized catalyst can be used in epoxide ring-opening reactions, especially when the epoxide is an epoxidized fatty acid ester, particularly those derived from plant oils. This general reaction scheme is as follows:

↜ = fatty acid chain
ROOC = alkyl ester of triglyceride ester

Exemplary functionalized plant oils for use in the invention include those derived from soybean, canola, camelina, corn, sunflower, peanut, and the like. Such epoxide ring-opening reaction may be carried out under relatively mild reaction conditions. For example, the reaction mixture including the catalyst may be maintained at a temperature of between about 20° C. to about 75° C. during the reaction.

In one embodiment, the acid-functionalized nanoparticle catalysts can be applied for the ring opening of epoxidized methyl oleate (EMO) in the production of soy polyols. As described in the examples below, reaction of the EMO with methanol in the presence of the nanoparticle catalysts yielded 100% selectivity on α-methoxy-hydroxy methyl oleate, an identical yield to nonrecyclable strong acid catalyst ($H_2SO_4$). Thus, a greener synthetic route for soy polyol production can be achieved using the nanoparticle catalyst with excellent atom economy, E factor, and dominance in nine environmental impacts over $H_2SO_4$ and commercial recyclable resin catalysts such as SAC 13 and Amberlyst 15. This synthetic strategy using the acid-functionalized nanoparticles may replace the use of non-recyclable homogeneous acid catalysts with several economic and environmental benefits to the practical industrial applications: 1) the core of the nanoparticles responds strongly to a magnet that can provide more convenient reaction and recycling processes in a magnetic field, 2) the siloxane coating enables great stability on the soy polyol process, and 3) high surface area provides very strong catalytic strength in the reaction comparable to $H_2SO_4$.

In another embodiment, the acid-functionalized nanoparticle catalysts can be used in the pre-treatment of biomass for cellulose release and cellulose hydrolysis to glucose and other C6 sugars, such as fructose. The biomass can be any cellulosic material, such as lignocellulosic material derived from wood, or other plant-based cellulose derived from plants including switchgrass hemp, corn, sorghum, or sugarcane. In cellulose hydrolysis reactions, the reaction mixture is generally maintained at a temperature of between about 100° C. to about 300° C., between about 150° C. to about 250° C., or between about 180° C. to about 225° C.

Following reaction, the nanoparticles comprising a ferromagnetic core, and especially Fe(0), can be separated from the reaction media and reused. Separation is achieved by exposing the reaction media to a magnetic field, such as through the use of a supermagnet. The nanoparticles rapidly precipitate and can be removed from the reaction media and recycled. The ferromagnetic metal core facilitates the magnetic isolation of the nanoparticles from the reaction media.

In certain aspects, complete removal of the iron-containing catalyst is very important, because iron (II/III) is a catalyst for Fenton-type radical reactions, which will decrease the lifetime of the materials that contain the iron residues. The use of nanoparticles comprising a ferromagnetic core results in virtually complete catalyst removal. Accordingly, hydrolyzed reaction products can be recovered which are substantially free of the catalyst. In contrast, catalysts without a strongly ferromagnetic core, such as iron oxide catalysts, cannot be completely removed by a magnetic field thereby resulting in a minor fraction of the catalyst remaining in the material.

EXAMPLES

The following examples set forth exemplary catalyst materials and reactions involving the same according to certain embodiments of the present invention. It is to be understood, however, that these examples are provided by way of illustration and nothing therein should be taken as a limitation upon the overall scope of the invention.

$Fe/Fe_3O_4$ nanoparticles may be synthesized via a number of different procedures. In one such procedure, monodisperse Fe nanoparticles are prepared then further reacted to provide an outer iron oxide shell. In other procedures, iron carbonyl, $Fe(CO)_5$, is reacted to yield a core/shell $Fe/Fe_3O_4$ nanoparticle. These synthesis schemes are discussed in greater detail below.

Example 1

A. Preparation of Monodisperse Fe Nanoparticles

Iron nanoparticles were prepared by extensive modification of a procedure described by Peng et al., *J. Am. Chem. Soc.*, 2006, 128, 10676-10677. 20 mL octadecene and 0.3 mL oleylamine were added to a 100 mL Schlenk flask and heated to 120° C. under Argon (Ar) for 30 minutes. After raising the temperature to 180° C., 0.7 mL $Fe(CO)_5$ was added under Ar. The solution turned black within 3 minutes and was kept at 180° C. for 20 minutes before cooling to room temperature. Under Ar, the supernatant was transferred to a centrifuge tube. Iron nanoparticles accumulated on the stir bar were washed with degassed hexane (3×10 mL) and combined with the supernatant. Next, 50 mL of degassed absolute ethanol was added and mixed thoroughly. Nanoparticles were collected by centrifugation (8000 rpm for 30 min). After decanting the clear solvent, the nanoparticles were re-dispersed into 15 mL degassed hexane and precipitated out by adding 20 mL of absolute ethanol. The product was dried under vacuum and stored under Ar for further use.

B. Preparation of Superparamagnetic Core/Shell $Fe/Fe_3O_4$ Nanoparticles 15 mL octadecene and 6 mg $(CH_3)_2NO$ were added into a 50 mL Schlenk flask, and after degassing by three freeze-pump-thaw cycles, the reaction container was refilled with Ar. The reaction mixture was kept at 130° C. for 30 minutes, then 80 mg iron nanoparticles in 2 mL of hexane were added via a syringe. After stirring at 130° C. for 2 hours, the mixture was heated to 250° C. and stirred at this temperature for another 30 minutes. Upon cooling to room temperature, the reaction mixture was transferred to a centrifuge tube and 25 mL isopropanol was added. The nanoparticles were collected by centrifugation (8000 rpm, 20 min). The obtained nanoparticles were re-dispersed into 5 mL hexane and precipitated out by adding 10 mL absolute ethanol. The product was dried under vacuum and stored under Ar for further use.

C. Preparation of APTES Coated $Fe/Fe_3O_4$ Nanoparticles 40 mg $Fe/Fe_3O_4$ nanoparticles were dispersed in 80 mL hexane. 0.40 mL 3-aminopropyltriethoxysilane (APTES) and 8 ml acetic acid (HOAc) were added and the reaction mixture was shaken at room temperature for 72 hours. The black-brown precipitate was collected by centrifugation (8000 rpm, 5 min). The obtained product was further washed with 5 mL of hexane 3 times. After drying under vacuum, 38 mg APTES-functionalized nanoparticles were obtained. The nanoparticles were characterized by measuring their zeta-potential, which was found to be +40±3 mV.

D. Preparation of TPTES Coated $Fe/Fe_3O_4$ Nanoparticles

Alternatively to C, the nanoparticles may be coated with 3-thiopropyltriethoxysilane (TPTES). 40 mg $Fe/Fe_3O_4$ nanoparticles were dispersed in 80 mL hexane. 0.40 mL TPTES and 8 ml acetic acid (HOAc) were added and the reaction mixture was shaken at room temperature for 72 hours. The black-brown precipitate was collected by centrifugation (8000 rpm, 5 min). The obtained product was further washed with 5 mL of hexane 3 times. After drying under vacuum, 38 mg TPTES-functionalized nanoparticles were obtained. The nanoparticles were characterized by measuring their zeta-potential, which was found to be +10±3 mV.

E. Preparation of Sulfamic Acid-Functionalized $Fe/Fe_3O_4$ Nanoparticles 30 mg APTES-coated $Fe/Fe_3O_4$ nanoparticles were dispersed in 15 mL dry methylene chloride in an ultrasonic bath (10 min of sonication). With a gentle stream of Ar, a solution of 0.1 mL chlorosulfuric acid in 1 mL of dry methylene chloride was added dropwise in 10 minutes. Nanoparticles were collected by centrifugation (8000 rpm, 5 min), and further washed consecutively with dry methylene chloride (3×5 mL) and tetrahydrofuran (THF) (3×5 mL). After drying under vacuum, 31 mg of nanoparticles were obtained. It is noted that the same procedure may also be used to with the TPTES-coated $Fe/Fe_3O_4$ nanoparticles.

Figure 4:
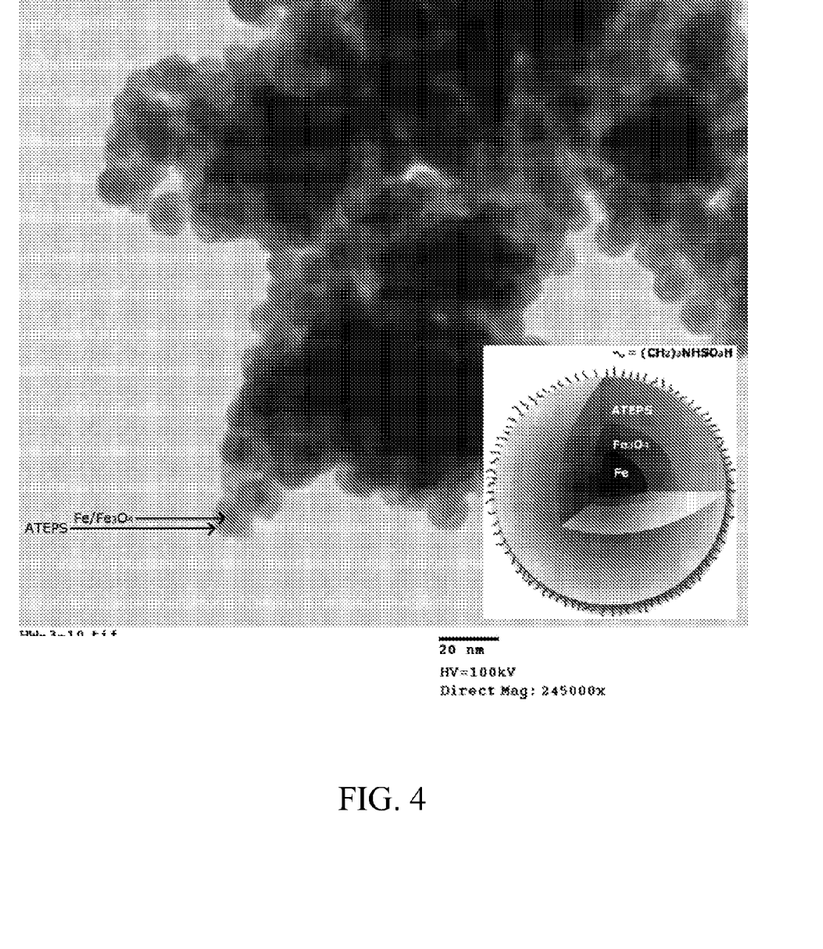
FIG. 4 is a TEM image of APTES-coated $Fe/Fe_3O_4$ nanoparticles bearing terminal sulfamic acid groups, along with an inset schematic depiction of the structure of the nanoparticles.

TEM images of the particles were recorded by using a Philips CM100 microscope 100 kV. As can be seen in FIG. 4, TEM imaging clearly showed spherical core/shell structure of the acid-functionalized nanoparticles. FIG. 4 also schematically depicts the overall particle structure. The average nanoparticle diameter was 3±1 nm, and the thickness of the acid-functionalized APTES coating was about 2 nm.

Dynamic light scattering (DLS) and zeta potential (ZP) measurements were carried out in distilled water by a Brookhaven Zeta-PALS with Bi-Mas particle sizing option. Based upon the DLS measurement, the sulfamic acid-functionalized $Fe/Fe_3O_4$ nanoparticles were found to be highly monodisperse (polydispersity=0.229). The effective diameter was around 58 nm. The different diameters between TEM and DLS measurements can be explained by clustering of the acid-functionalized nanoparticles in water used in the DLS measurement. Zeta potential measurement clearly indicated that the sulfamic acid-functionalized $Fe/Fe_3O_4$ nanoparticles carry negative charges on their surface. The zeta potential value was −30±2 eV, indicating the nanoparticles prepared by this method are stable in water. Because the terminal amine groups present after APTES functionalization carry positive charges, the recording of a stable negative potential is an indication for a high conversion ratio of the terminal amino to sulfamic acid groups.

Powder X-ray diffraction was used to characterize the composition of the core/shell nanoparticles. Cu-Kα radiation was used with a curved crystal graphite monochromator. The operating range for the X-ray target was 45 kV and 45 mA.

Figure 5:
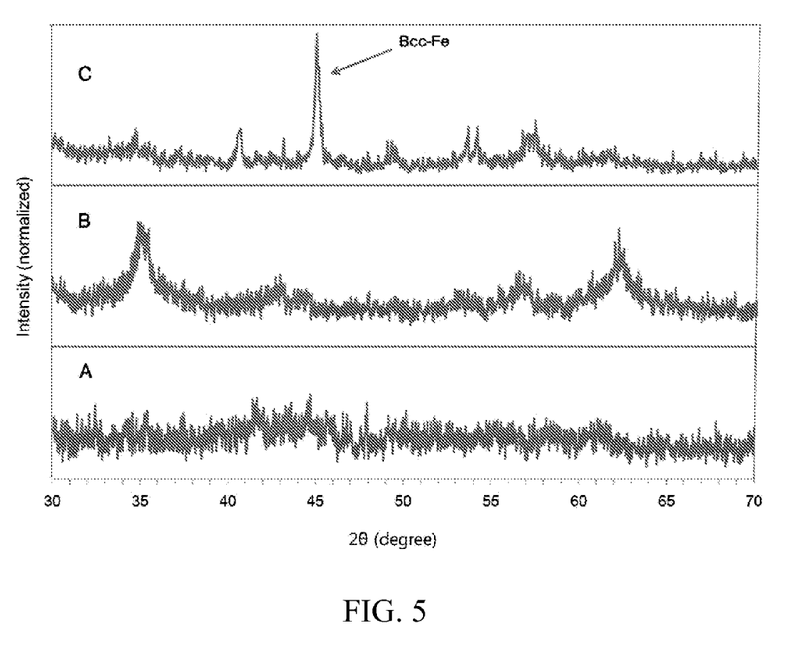
FIG. 5 shows XRD patterns of A) APTES-coated $Fe/Fe_3O_4$ nanoparticles, B) annealed APTES-coated $Fe/Fe_3O_4$ nanoparticles under Ar at 300 C for 2 h, C) annealed APTES-coated $Fe/Fe_3O_4$ nanoparticles under Ar at 400 C for 1 h.

The X-ray scans were in range of 20>2φ>70°. As shown in FIG. 5, the acid functionalized nanoparticles are amorphous as indicated by the absence of specific diffraction peaks in their X-ray diffraction (XRD) pattern (see, pattern "A"). Typical Fe diffraction peaks are observed after annealing the nanoparticles at 300° C. under argon for 2 h (see, pattern "B"), and further annealing of the nanoparticles at 400° C. under argon for 1 hour led to the appearance of a sharp bcc-Fe diffraction peak (see, pattern "C"). The XRD characterization gives more supportive data for the existence of $Fe/Fe_3O_4$ core/shell structure as indicated by the TEM image. Acid loading of the nanoparticle (0.36 mmol g) was determined by acid-base titration according to Peng et al.

F. Preparation of Carboxylic Acid-Functionalized $Fe/Fe_3O_4$ Nanoparticles 30 mg APTES coated $Fe/Fe_3O_4$ nanoparticles were dispersed in 15 mL dry methylene chloride in an ultrasonic bath (10 min. of sonication). 1 mL of dimethylformamide (DMF) was added. Under a gentle stream of Ar, a solution 1.0 mL of succinic acid anhydride ($C_4H_4O_2$) or glutaric acid anhydride ($C_5H_6O_3$) or adipic acid anhydride ($C_6H_8O_3$) or heptanedioic acid anhydride ($C_7H_{10}O_3$) was added at once. The mixture was allowed to react at room temperature for 2 h, redispersed by 10 min. of sonication, and again allowed to react for 2 h. Nanoparticles were collected by centrifugation (8000 rpm, 5 min), and further washed consecutively with dry methylene chloride (3×5 mL), and tetrahydrofuran (THF) (3×5 mL). After drying under vacuum, 28-30 mg of nanoparticles were obtained. It is noted that the same procedure may also be used to with the TPTES-coated $Fe/Fe_3O_4$ nanoparticles.

G. Preparation of Sulfonic Acid-Functionalized $Fe/Fe_3O_4$ Nanoparticles 30 mg APTES coated $Fe/Fe_3O_4$ nanoparticles were dispersed in 15 mL dry methylene chloride in an ultrasonic bath (10 min. of sonication). Under a gentle stream of Ar, a solution of 50 mg of propane-sultone or butane-sultone in 1 mL of dry methylene chloride was added dropwise during 10 min. Nanoparticles were allowed to react for 1 h at RT and then collected by centrifugation (8000 rpm, 5 min), and further washed consecutively with dry methylene chloride (3×5 mL), and tetrahydrofuran (THF) (3×5 mL). After drying under vacuum, 27-29 mg of nanoparticles were obtained. It is noted that the same procedure may also be used to with the TPTES-coated $Fe/Fe_3O_4$ nanoparticles.

Example 2

In this example, alternate methods of preparing superparamagentic core/shell $Fe/Fe_3O_4$ nanoparticles are described.

Figure 6:
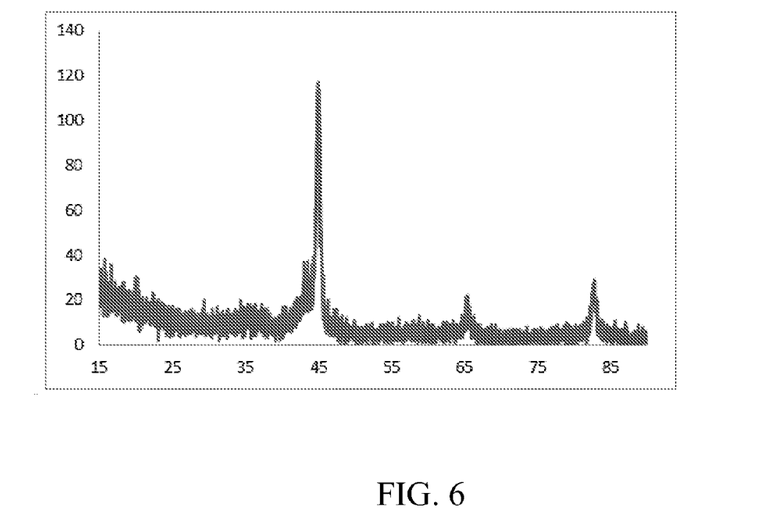
FIG. 6 is an XRD of $Fe/Fe_3O_4$ nanoparticles using 1-methyl-3-tetradecylimidazolium bromide as an additive.
Figure 7:
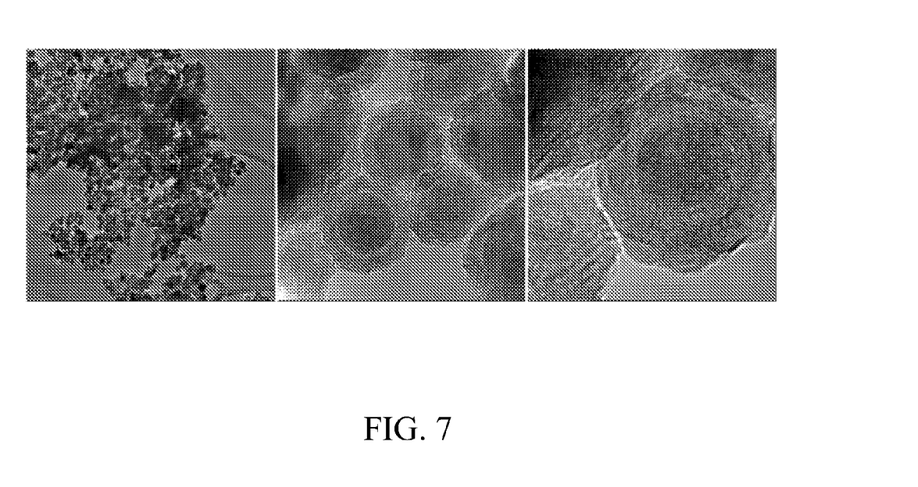
FIG. 7 depicts TEM and HRTEM images of the $Fe/Fe_3O_4$ nanoparticles using 1-methyl-3-tetradecylimidazolium bromide as an additive.

A. Preparation of $Fe/Fe_3O_4$ Nanoparticles Using $Fe(CO)_5$ and 1-Methyl-3-Tetradecylimidazolium Bromide A 500 mL three necked round-bottom-flask equipped with mechanical stirrer, cold water jacked condenser, and temperature probe was charged with 250 mL octyldecene, 3.75 mL oleylamine, 4.48 g 1-methyl-3-tetradecylimidazolium bromide. The reaction mixture was degassed with argon flow at 160° C. for 30 min, and then heated to 200° C. 10 mL of $Fe(CO)_5$ was added via a syringe within 2 min. The reaction mixture was kept at 200° C. with stirring for another 40 min. Upon cooling to room temperature, nanoparticles were collected by centrifugation. After washing with hexane and ethanol, the obtained product was dried in vacuum and stored at room temperature. Based on iron, the yield of the reaction is 87%. The XRD characterization of the nanoparticles provided as FIG. 6 showed the characteristic diffraction peaks of bcc-Fe. Moreover, TEM clearly revealed the core/shell structure of the nanoparticle, with core diameter of 8 nm and shell thickness of 3 nm, HRTEM showed that the nanoparticles assume multi-crystallinity (FIG. 7).

The $Fe/Fe_3O_4$ nanoparticles can then be coated with APTES or TPTES and functionalized as described in Example 1.

Figure 8:
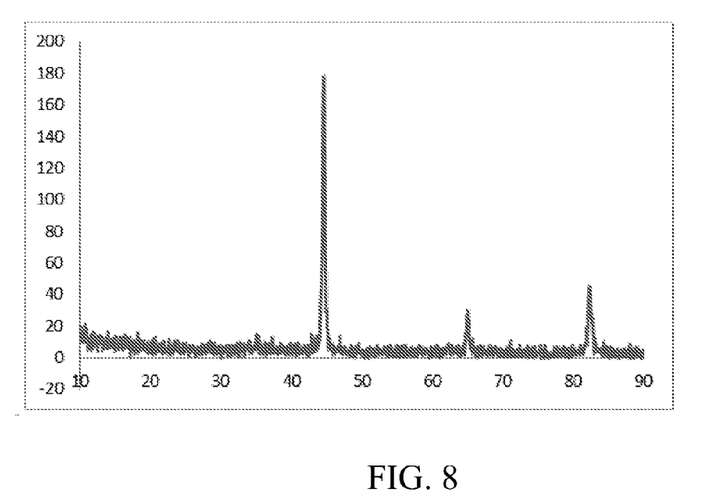
FIG. 8 is an XRD of $Fe/Fe_3O_4$ nanoparticles using didodecyldimethyl-ammonium bromide as an additive.
Figure 9:
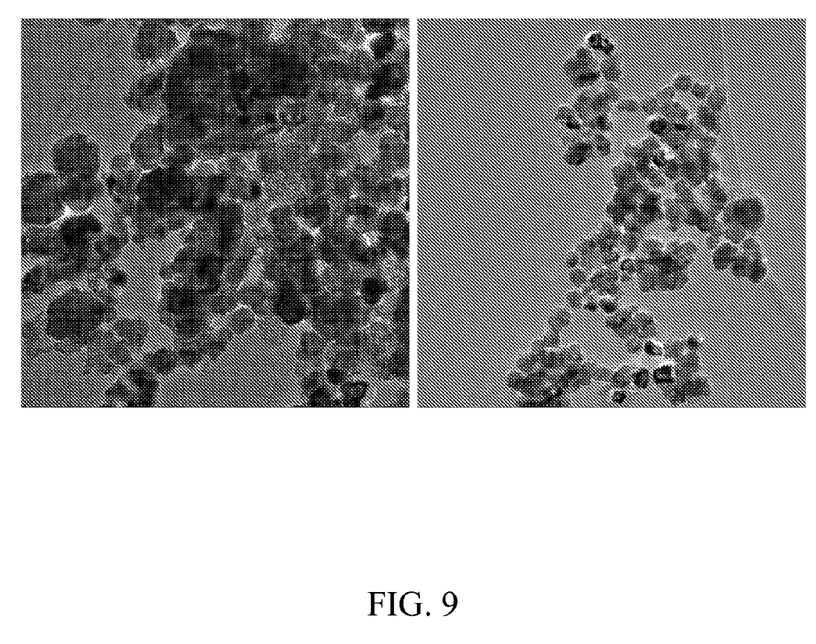
FIG. 9 is a TEM image of $Fe/Fe_3O_4$ nanoparticles using didodecyldimethyl-ammonium bromide as an additive.

B. Preparation of $Fe/Fe_3O_4$ Nanoparticles Using $Fe(CO)_5$ and Didodecyldimethyl-Ammonium Bromide Under the same reaction conditions used in synthesis scheme A above, using didodecyldimethyl-ammonium bromide as additive resulted in Fe(0) nanoparticles as shown by the XRD characterization of FIG. 8. TEM characterization revealed that the diameter of obtained nanoparticles is between 20-25 nm. FIG. 9 is a TEM of the $Fe/Fe_3O_4$ nanoparticles produced according to this process. The $Fe/Fe_3O_4$ nanoparticles can then be coated with APTES or TPTES and functionalized as described in Example 1.

Example 3

This example describes alternate methods of providing an acid functionalized siloxane coating on the nanoparticles.

A. Preparation of Sulfonic Acid-Functionalized Mercaptosiloxane-Coated $Fe/Fe_3O_4$ Nanoparticles Using $Fe(CO)_5$ in Oleylamine and Octadecene $Fe/Fe_3O_4$ nanoparticles prepared as described in A and B of Example 1. The formed nanoparticles were precipitated by applying a strong magnet, and the supernatant was decanted under the protection of argon stream. The collected nanoparticles were washed several times with hexane to remove the excess ligands. 200 mg of the $Fe/Fe_3O_4$ nanoparticles were reacted with 0.4 mL of 3-mercaptopropyl-trimethoxysilane and 10 µL of acetic acid. After washing with hexane, ethanol and methanol, $H_2O_2$ was added. The formed nanoparticles were again purified by subsequent water washings and sonicated with $H_2SO_4$ for 10 min. The final product was further washed with water, and dried under high vacuum. The acid loading was determined by acid/base titration and was found to be 0.33 mmol/g.

B. Preparation of Sulfonic Acid-Functionalized Mercaptosiloxane-Coated $Fe/Fe_3O_4$ Nanoparticles Using $Fe(acac)_3$ In another approach tris(acetylacetonato) iron(III) (Fe (acac)$_3$) was mixed in phenyl ether with oleic acid and oleylamine. Then, 1,2-hexadecanediol was added, and the formed solution was refluxed. Upon cooling ethanol was added, and a dark brown precipitate form, which was separated by centrifugation. The collected nanoparticles were further washed with ethanol to remove the excess ligands. After re-dispersing in hexane by sonication, 200 mg of the $Fe/Fe_3O_4$ nanoparticles were reacted with 0.4 mL of 3-mercaptopropyl-trimethoxysilane and 10 µL of acetic acid. The formed nanoparticles were collected by a magnet, washed with hexane and ethanol, and then re-dispersed in a mixture of water and methanol. 30% $H_2O_2$ was added in an ice-bath and the formed nanoparticles were collected by centrifugation, washed with water and sonicated in 1M $H_2SO_4$. The collected nanoparticles were further washed with water and dried under high vacuum.

TEM revealed that the average diameter of the acid functionalized nanoparticles was between about 10 to 12 nm, and that the nanocomposite comprised a core/shell structure. The high density core indicated the presence of Fe(0), which renders the high magnetization property of this nanomaterial. Dynamic light scattering (DLS) indicated that the hydrodynamic diameter of the acid functionalized nanoparticles is about 60 nm. The nanoparticles are monodisperse with a polydispersity of 0.22. Zeta potential of the acid-functionalized nanoparticles is −29.28 mV, indicating sufficient coating with sulfonic acid groups on the surface of the nanoparticles.

Example 4

α-Methoxy-Hydroxylation of EMO Using Sulfamic Acid-Functionalized APTES-Coated Fe/Fe$_3$O$_4$ Nanoparticles Epoxidized methyl oleate (EMO) was used as a model for epoxidized soybean oil (ESO) to avoid the complexity of macromolecules in NMR and ESI-MS analysis. Epoxidized fatty acid methyl ester (EFAME) was obtained from FuJian ZhiShang Biomass Material Co., Ltd (Fujian, China). After purifying EFAME (yellow) through column chromatography (hexane/ethyl acetate gradient 99/1 to 90/10), epoxidized methyl oleate (EMO) (clear) was obtained. The sulfamic acid-functionalized iron nanoparticles from Example 1 and H$_2$SO$_4$ were used for ring opening of EMO as a comparison to the commercial resin catalysts (SAC 13 and Amberlyst 15) reported by Rio et al. EMO was agitated in methanol (10 mass equivalents) with 10 w/w % of the nanoparticles and H$_2$SO$_4$, respectively. The procedure for each comparison is described below.
1) Mixture of EMO 0.2 g (0.64 mmol), the nanoparticles 0.02 g, methanol 0.2 g (6.40 mmol) was agitated for 30 minutes at 40° C.
2) Mixture of EMO 0.2 g (0.64 mmol), H$_2$SO$_4$ 0.02 g, methanol 0.2 g (6.40 mmol) was agitated for 30 minutes at room temperature.
3) EMO 0.2 g (0.64 mmol), SAC 13 0.02 g, methanol 0.2 g (6.40 mmol) for 60 minutes at 60° C.
4) EMO 0.2 g (0.64 mmol), Amberlyst 15 0.02 g, methanol 0.2 g (6.40 mmol) for 100 minutes at 60° C.

Figure 10:
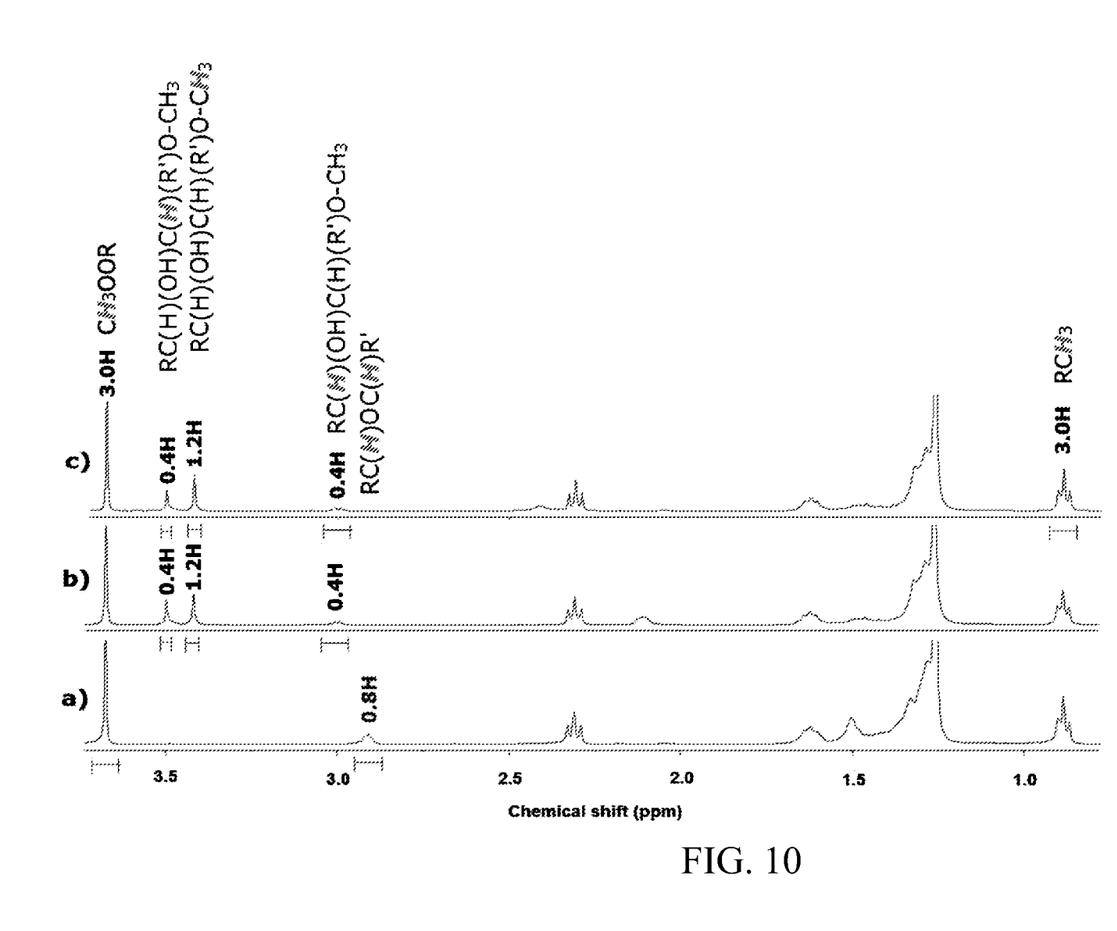
FIG. 10 depicts $^1H$ NMR traces of a) EMO, b) α-methoxyhydroxylation of EMO by the sulfamic acid-functionalized $Fe/Fe_3O_4$ nanoparticles, and c) α-methoxyhydroxylation of EMO by $H_2SO_4$.

The atom economy (the mass percentage of atoms from reactants that appear in the desired product of a balanced reaction equation) and E factor (the ratio of mass of waste over mass of product) were evaluated using quantitative NMR analysis. $^1$H NMR spectra for the samples were recorded quantitatively using a Varian Unity 400 MHZ spectrometer (Varian Inc, Palo Alto, Calif.) on a 5 mm penta probe. For $^1$H NMR experiments, sample solutions were prepared in CDCl$_3$. Trace a) of FIG. 10 is for EMO, trace b) shows the α-methoxyhydroxylation of EMO by the sulfamic acid-functionalized Fe/Fe$_3$O$_4$ nanoparticles, and trace c) shows the α-methoxyhydroxylation of EMO by H$_2$SO$_4$. For ESI-MS, spectra were acquired on an API4000 (Applied Biosystems, Foster City, Calif.) triple quadrupole mass spectrometer with electrospray ionization (ESI). An aliquot of 2-10 μl in 1.0 ml methanol was presented to the ESI needle at 30 μl/min. The mass analyzers were adjusted to a resolution of 0.7 μm full width at half height. Twenty continuum scans were averaged in multiple channel analyzer (MCA) mode. The scan speed was 100 u/s. The source temperature (heated nebulizer) was 100° C., the interface heater was on, −4.5 kV were applied to the electrospray capillary, the curtain gas was set at 20 (arbitrary units), and the two ion source gases were set at 45 (arbitrary units). The declustering potential was −90 V, and the entrance potential was −12. $^1$H-$^1$H COSY NMR and ESI-MS revealed the scaffold of α-methoxyhydroxylation of EMO.

As a result, the reaction efficiency of sulfamic acid functionalized Fe/Fe$_3$O$_4$ nanoparticles was comparable to that of sulfuric acid; the nanoparticles produced identically clean product to H$_2$SO$_4$ with reduced reaction time (30 min) at lower temperature (40° C.) than published data using solid catalysts of SAC 13 (60 min at 60° C.) and Amberlite 15 (100 min at 60° C.). See, Rios et al. The nanoparticles also showed excellent atom economy with, as for H$_2$SO$_4$, 100% yield compared with SAC 13 (yield: 83%) and Amberlite 15 (yield: 87%) from NMR integration using a methyl group (3H) at δ 3.67 and 0.89 as a quantitative internal standard. The oxirane ring (0.8H) was completely converted to α-methoxy (0.4H) [RC(H)(OH)C(H)(R')O—CH3] signal at δ 3.49 coupled with vicinity hydroxyl (0.4H) [RC(H)(OH)C(H)(R')O—CH3] signal at δ 3.00. Methyl site (1.2H) of α-methoxy was also shown at δ 3.42. $^1$H-$^1$H COSY NMR showed a clear cross peak between α-methoxy and its vicinal hydroxyl. ESI-MS revealed the only presence of α-methoxyhydroxylation (m/z=367.2) without ketone byproduct (m/z=335.5).

Figure 11:
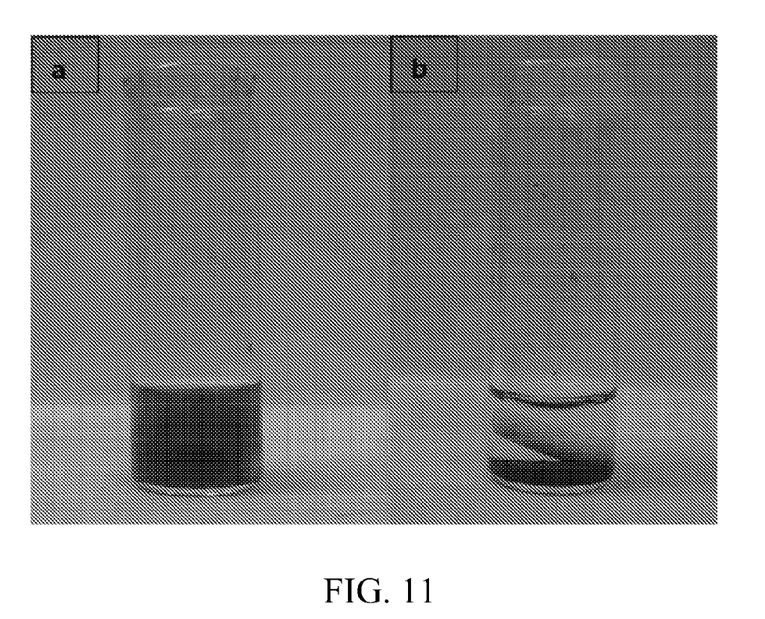
FIG. 11 depicts photographs a) right after the α-methoxyhydroxylation of EMO of the nanoparticles in the reaction solution, and b) 5 min after the solution was placed on a supermagnet.

In terms of recycling efficiency, the nanoparticles were observed to precipitate in 5 minutes on a supermagnet. FIG. 11a is an image of the nanoparticles in the reactant solution right after reaction, and FIG. 11b shows the solution after being placed on the supermagnet. Also, the recycled nanoparticles have shown a steady 100% epoxy ring-opening conversion and 100% selectivity of α-methoxy-hydroxylation in 5 consecutive uses. Thus, it was confirmed that the nanoparticles provided not only excellent catalysis, on par with H$_2$SO$_4$, but also environmental benefits deriving from their recyclability.

Life Cycle Assessment on the Syntheses of the Soy Polyol

Life cycle assessment (LCA) is an important tool that allows evaluation of the environmental impacts associated with a chemical process or a material's entire life cycle; however, research is limited that integrates a comprehensive LCA, and the scope of environmental impacts and unknowns presents a significant challenge. Using renewable resources is merely one of the 12 principles of green chemistry, so biobased materials scientists and engineers need more comprehensive LCA to designate their processes as properly green. The practical development of greener solutions will become more prevalent as awareness of environmental concerns increases. Multivariate metrics used in LCAs to assess environmental impacts are informative to determine overall greenness. For this example, LCA based on nine environmental impact metrics was conducted to select the greenest synthesis from the four different catalysts (the nanoparticles, H$_2$SO$_4$, SAC 13, and Amberlite 15). The reaction impact assessment for epoxide ring opening was conducted using a procedure based on the ISO lifecycle assessment method, an approach that includes both the amount of waste as well as the harmfulness of the waste. The four reactions were compared with respect to nine environmental risks: acidification potential (AP), ozone depletion potential (ODP), smog formation potential (SFP), global warming potential (GWP), human toxicity by ingestion (INGTP), human toxicity by inhalation (INHTP), persistence (PER), bioaccumulation (ACCU), and abiotic resource depletion potential (ADP). For most of these risks, the chemical outputs are compared with reference chemicals, which allow addition of all contributors to the risk for comparison within a synthetic route as well as between routes. A multimedia compartmental model (MCM) was built to assess the partitioning behavior of each chemical into four environmental compartments (air, water, soil, and sediment). This was implemented in assessing the human toxicity risk of each procedure. The results are given in Table 1. Values are expressed in kilograms of reference compound. Persistence (PER) and bioaccumulation (ACCU) refer to the maximum persistence or bioaccumulation of any species in the particular process. Bioaccumulation is expressed in terms of bioconcentration factor.

TABLE 1

Comparison of the Overall Indices (I) For All Four Routes

| Route | $I_{AP}$ | $I_{ODP}$ | $I_{SFP}$ | $I_{GWP}$ | $I_{INHTP}$ | $I_{INGTP}$ | PER, $t_{1/2}$ | ACCU | $I_{ADP}$ |
|---|---|---|---|---|---|---|---|---|---|
| Nanoparticles | 0 | 0 | $1.49 \times 10^{-4}$ | $5.28 \times 10^{-2}$ | $4.70 \times 10^{-5}$ | 0.824 | 24 d | 1 | 0 |
| $H_2SO_4$ | 0 | 0 | $1.49 \times 10^{-4}$ | $4.92 \times 10^{-2}$ | $4.70 \times 10^{-5}$ | 89.3 | 24 d | 1 | $1.0 \times 10^{-5}$ |
| SAC13 | 0 | 0 | $1.79 \times 10^{-4}$ | $6.94 \times 10^{-2}$ | $5.70 \times 10^{-5}$ | 0.993 | weeks | $7.3 \times 10^5$ | 0 |
| Amberlyst | 0 | 0 | $1.17 \times 10^{-4}$ | $6.58 \times 10^{-2}$ | $5.43 \times 10^{-5}$ | 0.947 | weeks | $7.3 \times 10^5$ | 0 |

The ring opening of EMO via the four processes poses a relatively small set of environmental concerns, but the low energy requirements and high yield of the nanoparticle process according to the present invention set it ahead of the other processes. In addition, recovery and reusability of the iron nanoparticles would likely be less involved than recovery of the conventional catalysts, SAC13 and Amberlyst. The global warming risk is lowest with the nanoparticle and $H_2SO_4$ routes, mainly due to the lower reaction temperature and slight solvent reduction manifested in the distillation contribution. The inhalation risk of all processes is similar, biased mainly by the increased solvent use in the conventional catalysts for byproduct purification. The ingestion toxicity risk is very high for the $H_2SO_4$ route because of the environmental release of sulfuric acid. The risk of releasing environmentally persistent chemicals is similar for all reactions, an average half-life on the order of several weeks. Potential for bioaccumulation by the ketone byproduct of the conventional catalyst routes is significant. Although no significant resource depletion occurred, sulfur does have documented abiotic resource depletion potential. Overall, the environmental impacts are relatively similar across the board, but the nanoparticles route is superior or equal to the competing routes with respect to every risk factor.

Example 5

Sulfamic Acid-Functionalized Fe/Fe$_3$O$_4$ Nanoparticle Catalyzed Hydrolysis of Cellulose The sulfamic acid-functionalized nanoparticles from Example 1 were used as a catalyst material in the pretreatment of biomass for cellulose release and hydrolysis. It was discovered that the magnetic, acid-functionalized nanoparticles have enough acidity to pre-treat biomass for cellulose release and hydrolyze cellulose to glucose and other C6 sugars. Moreover, the density of the nanoparticles permits them to be suspended in the biomass solution to insure the nanoparticles react with biomass. The magnetic qualities of the nanoparticles also makes them easily separated from the biomass solution by applying a magnetic field and made available for reuse.

Cellulose and acid-functionalized Fe/Fe$_3$O$_4$ nanoparticles were dispersed in water by sonication. In a high-pressure reactor, the reaction mixture was maintained at 180° C. for 12 hours. After cooling to room temperature, the acid-functionalized Fe/Fe$_3$O$_4$ was separated easily with a small magnet. The liquid phase was decanted for HPLC analysis, whereas the magnet-collected solid was washed with water and 1M $H_2SO_4$. The recycled catalyst showed the same catalytic reactivity when re-subjected to the reaction.

Figure 12:
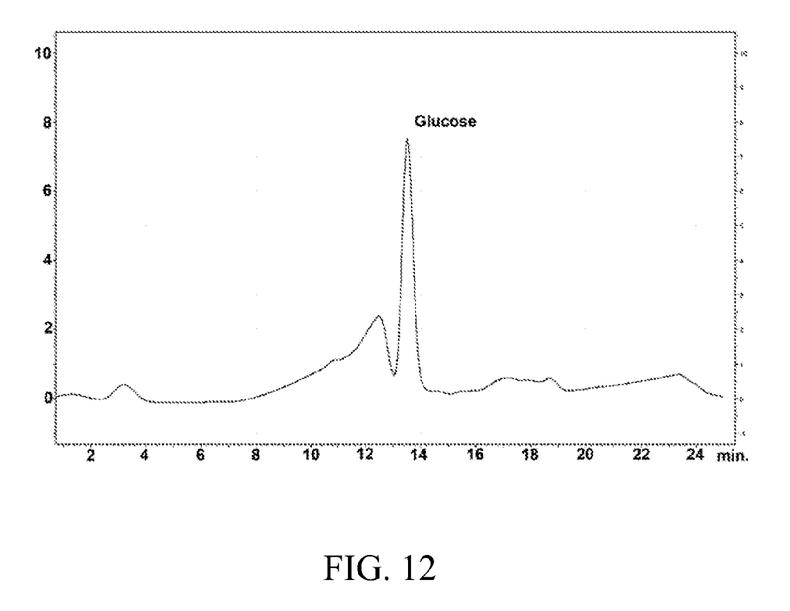
FIGS. 12 and 13 provide HPLC data for cellulose conversion using $H_2SO_4$ and $Fe/Fe_3O_4$/sulfamic acid-functionalized nanoparticles, respectively.
Figure 13:
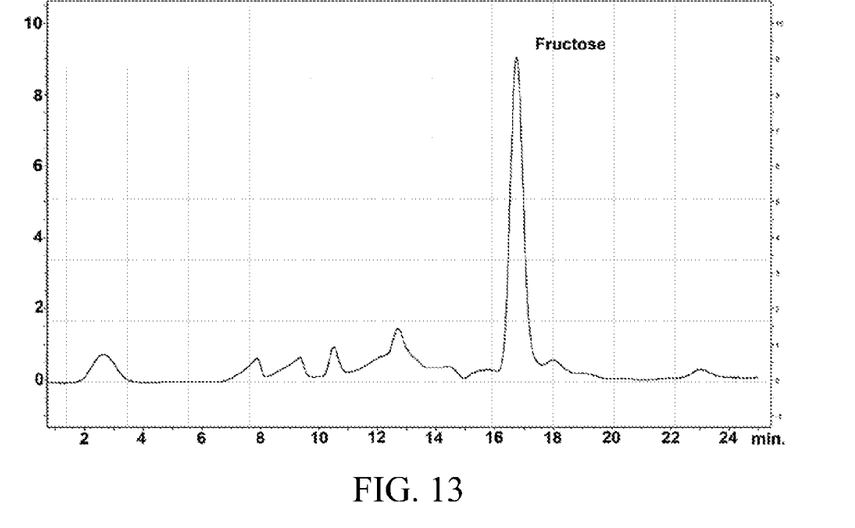

HPLC data in FIG. 12 indicates that a $H_2SO_4$ catalyzed reaction mainly forms glucose. However, the acid-functionalized Fe/Fe$_3$O$_4$ nanoparticle catalyzed reaction mainly forms fructose. See, FIG. 13. The reaction became very sluggish when the temperature decreased to 100° C.

Figure 14:
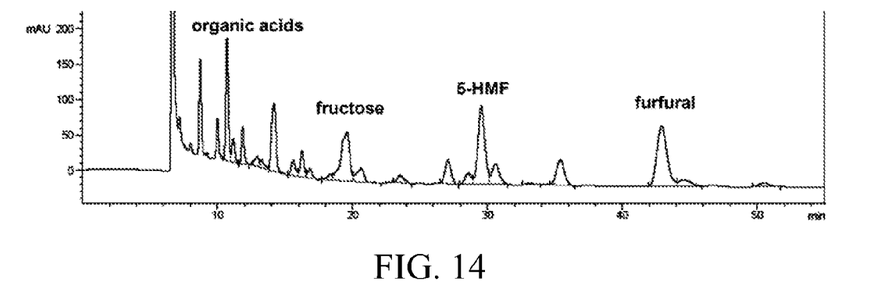
FIGS. 14 and 15 are graphs showing cellulose degradation products for reactions catalyzed by $H_2SO_4$ and $Fe/Fe_3O_4$/sulfamic acid-functionalized nanoparticles, respectively.
Figure 15:
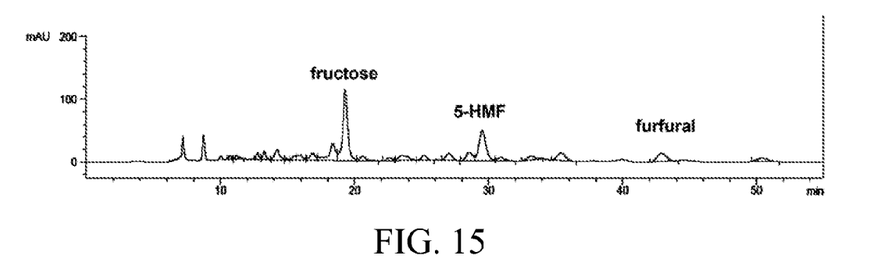

When reaction temperature was increased to 220° C. for 12 hours at pH 2.0, HPLC analysis of the reaction products from $H_2SO_4$ catalyzed reaction (FIG. 14) shows greater degradation products were generated than the acid-functionalized Fe/Fe$_3$O$_4$ nanoparticle catalyzed reaction (FIG. 15).

We claim:
1. A catalyst comprising:
   a plurality of nanoparticles comprising a ferromagnetic core and a metal oxide shell covering at least a portion of the outer surface of said core;
   a siloxane compound having a nucleophilic functional group at least partially coating said nanoparticles, said nucleophilic functional group having an acidic functional group attached thereto.
2. The catalyst according to claim 1, wherein said ferromagnetic core comprises a member selected from the group consisting of iron, nickel, cobalt, and alloys thereof.
3. The catalyst according to claim 1, wherein said metal oxide shell comprises a metal oxide selected from the group consisting of the oxides of Ag, Cu, Co, Fe, Mn, and Ni.
4. The catalyst according to claim 1, wherein said siloxane compound is an aminofunctional siloxane or a mercaptofunctional siloxane.
5. The catalyst according to claim 4, wherein said aminofunctional siloxane compound comprises 3-aminopropyltriethoxysilane (APTES), and said mercaptofunctional siloxane comprises 3-thiopropyltriethoxysilane (TPTES).
6. The catalyst according to claim 1, wherein said nanoparticles have an average particle diameter of between about 1 to about 100 nm.
7. The catalyst according to claim 1, wherein said nanoparticles have an average Brunauer-Emmett-Teller (BET) multipoint surface area of about 20 m$^2$/g to about 500 m$^2$/g.
8. The catalyst according to claim 1, wherein said acidic functional group is selected from the group consisting of sulfamic acid, carboxylic acids, and sulfonic acid.
9. The catalyst according to claim 8, wherein said acid is a carboxylic acid selected from the group consisting of succinic acid, glutaric acid, adipic acid, heptanedioic acid, and combinations thereof.
10. A method of protonating an oxygen atom involved in a carbon-oxygen bond in an organic compound comprising:
    providing a mixture comprising an organic compound having one or more carbon-oxygen bonds and a catalyst according to claim 1; and
    subjecting said mixture to conditions in which at least one oxygen atom involved in one of said carbon-oxygen bonds is protonated thereby forming a hydrolyzed product.
11. The method according to claim 10, wherein said organic compound is an epoxidized fatty acid ester.

12. The method according to claim 11, wherein said epoxidized fatty acid ester comprises epoxidized soybean oil.

13. The method according to claim 12, wherein said mixture further comprises methanol.

14. The method according to claim 12, wherein said mixture is reacted at a temperature of between about 20° C. to about 75° C.

15. The method according to claim 12, wherein said hydrolyzed product is a methoxylated soy polyol.

16. The method according to claim 10, wherein said organic compound comprises cellulose.

17. The method according to claim 16, wherein said mixture is reacted at a temperature of between about 100° C. to about 300° C.

18. The method according to claim 16, wherein said hydrolyzed product comprises a C6 sugar.

19. The method according to claim 16, wherein said hydrolyzed product comprises 5-hydroxymethyl-furfural (5-HMF).

20. The method according to claim 10, wherein, following protonation of said at least one oxygen atom, said method further comprises subjecting said mixture to a magnetic field so as to separate said catalyst therefrom.

\* \* \* \* \*